(12) United States Patent
Katti et al.

(10) Patent No.: US 11,541,150 B2
(45) Date of Patent: Jan. 3, 2023

(54) BLOCK-SCAFFOLDS FOR BONE REGENERATION USING NANO-CLAY POLYMER SCAFFOLDS

(71) Applicant: NDSU RESEARCH FOUNDATION, Fargo, ND (US)

(72) Inventors: Kalpana S. Katti, Fargo, ND (US); Dinesh Ramanath Katti, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 41 days.

(21) Appl. No.: 16/260,451

(22) Filed: Jan. 29, 2019

(65) Prior Publication Data
US 2019/0255221 A1    Aug. 22, 2019

Related U.S. Application Data

(63) Continuation of application No. PCT/US2017/044422, filed on Jul. 28, 2017.

(60) Provisional application No. 62/368,934, filed on Jul. 29, 2016.

(51) Int. Cl.
| | |
|---|---|
| *A61L 27/46* | (2006.01) |
| *A61L 27/54* | (2006.01) |
| *A61L 27/58* | (2006.01) |
| *C12N 5/00* | (2006.01) |

(52) U.S. Cl.
CPC ............... *A61L 27/46* (2013.01); *A61L 27/54* (2013.01); *A61L 27/58* (2013.01); *C12N 5/00* (2013.01); *A61L 2300/414* (2013.01); *A61L 2420/02* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 8,263,103 B2 | 9/2012 | Zhong | |
| 2003/0114936 A1* | 6/2003 | Sherwood | ........... A61F 2/30942 623/23.58 |
| 2009/0149948 A1 | 6/2009 | Atanasoska et al. | |
| 2009/0169524 A1* | 7/2009 | Katti | ....................... A61K 33/12 424/93.7 |
| 2011/0288223 A1 | 11/2011 | Kannan et al. | |
| 2013/0211543 A1 | 8/2013 | Chen et al. | |

FOREIGN PATENT DOCUMENTS

WO    2015170075 A2    11/2015

OTHER PUBLICATIONS

NDSU Research Foundation, PCT/US2017/044422 Filed Jul. 28, 2017, "Written Opinion of the International Searching Authority", 7 pages, dated Oct. 12, 2017.

Gunasingh et al., "Studies on Mechanical, Thermal properties and Characterization of Nanocomposites of Nylon-6-Thermoplastics Poly Urethane Rubber [TPUR] blend", Journal of Applied Chemistry, vol. 4, Issue 1, pp. 65-75, Mar. 2013.

Ambre et al., "Biomineralized hydroxypatite nanoclay composite scaffolds with polycaprolactone for stem cell-based bone tissue engineering", J Biomed Mater Res, Part A, vol. 103A, Issue 6, pp. 2077-2101, Jun. 2015.

Ambre et al., "Nanoclay Based Composite Scaffolds for Bone Tissue Engineering Applications", Journal of Nanotechnology in Engineering and Medicine, vol. 1, 9 pages, Aug. 2010.

Ambre et al., "In situ mineralized hydroxyapatite on amino acid modified nanoclays on novel bone biomaterials", Materials Science and Engineering C, vol. 31, pp. 1017-1029, 2011.

Katti et al., "Use of unnatural amino acids for design of novel organomodified clays as components of nanocomposite biomaterials", Phil. Trans. R. Soc. A., vol. 368, pp. 1963-1980, 2010.

Katti et al., "Molecular interactions in biomineralized hydroxyapatite amino acid modified nanoclay: In silico design of bone biomaterials", Materials Science and Engineering C, vol. 46, pp. 207-217, 2015.

* cited by examiner

*Primary Examiner* — Jessica Worsham
(74) *Attorney, Agent, or Firm* — McKee, Voorhees & Sease, PLC

(57) ABSTRACT

The invention relates to compositions useful for bone repair and methods of preparing the same. The invention is particularly suitable for bone repair of large bone defects. In an aspect of the invention, the compositions comprise a biocompatible polymer and a clay that form a scaffold. In a further aspect of the invention, the multiple scaffolds can be configured together to form scaffold blocks.

19 Claims, 20 Drawing Sheets

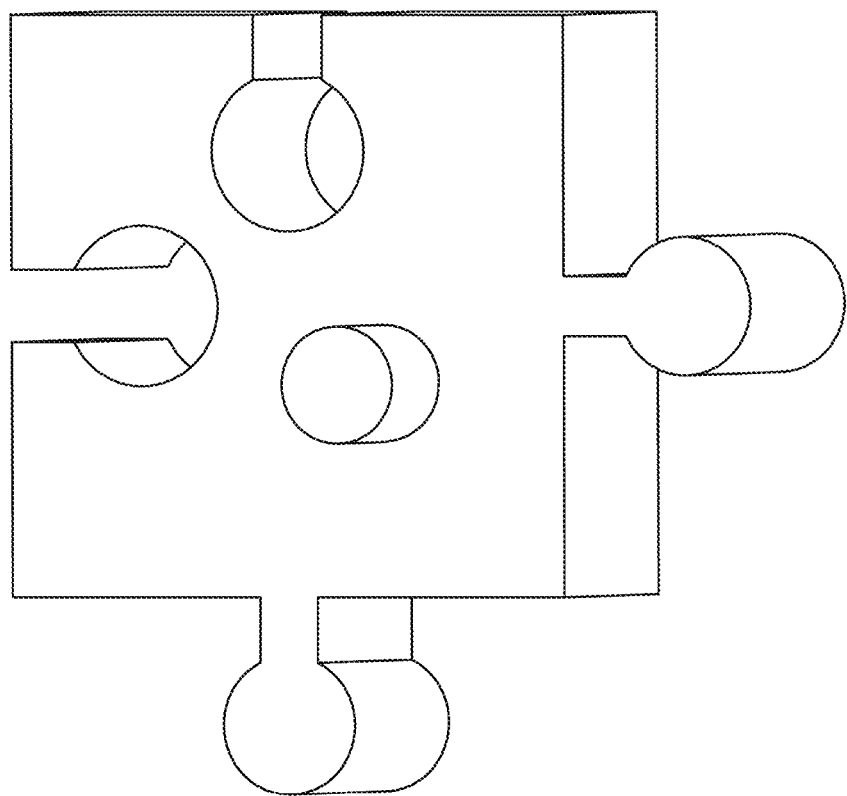

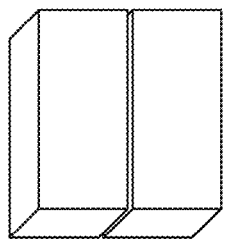
FIG. 5B
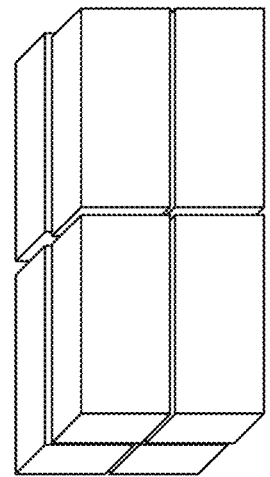
FIG. 5D
FIG. 5A
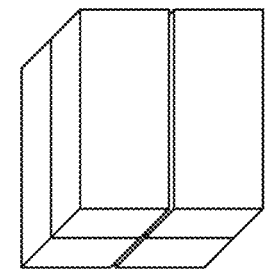
FIG. 5C

BLOCK-SCAFFOLDS FOR BONE REGENERATION USING NANO-CLAY POLYMER SCAFFOLDS

CROSS-REFERENCE TO RELATED APPLICATIONS

This application is a by-pass Continuation Application of PCT/US17/44422, filed Jul. 28, 2017, which claims priority under 35 U.S.C. § 119 to U.S. Provisional Application Ser. No. 62/368,934 filed on Jul. 29, 2016 and entitled "BLOCK-SCAFFOLDS FOR BONE REGENERATION USING NANO-CLAY POLYMER SCAFFOLDS." The entire contents of these patent applications are hereby expressly incorporated herein by reference including, without limitation, the specification, claims, and abstract, as well as any figures, tables, or drawings thereof.

FIELD OF THE INVENTION

The invention relates to compositions useful for bone repair and methods of preparing the same. The invention is particularly suitable for bone repair of large bone defects.

BACKGROUND OF THE INVENTIONS

A significant number of people require bone defect-related medical treatments each year. These treatments can be due to bone fractures or disorders and medical conditions that affect bone tissue. Further, the incidence of bone disorders and conditions has increased in recent years and is expected to continue to increase. Bone defect-treatments are not limited to humans, but also affect animals.

Fractures can vary from minor fractures requiring little medical attention to severe fractures requiring surgery and other extensive treatments. Severe fractures that encompass significant bone loss, crushing or multiple fractures do not self-heal (nonunion bone defects) and require surgical procedures to repair the bone defect. Nonunion bone defects are found more often in victims of trauma such as car accidents, farming and industrial accidents, war injuries, and sports injuries, for example, where it is reported that over 50% of bone fractures in the proximity of open wounds and 10% of fractures as a result of internal injuries are nonunion type bone defects. Nonunion bone defects are more complex, and require substantially more healing time, have a greater chance of near-term and long-term complications, and carry a disproportional amount of expense as compared with the 'simpler' fractures. Existing treatments for bridging of nonunion bone defects include the use of metallic plates, rods, and screws or by grafting bone tissue from other regions of the body, from a cadaver, or an animal. For the patient to return to normal functionality it is important for the patient to have as near as possible a restoration of structural integrity of the injured bone. These existing procedures, e.g., use of metallic inserts or grafted bone, have limitations and downsides.

Metallic inserts can have issues with stress shielding where the mismatch of mechanical properties can cause deterioration of surrounding bone, problems with anchoring (especially in cases where bone fragmentation occurs, and where anchoring is most crucial), higher risks of infections, chronic pain, issues with long-term performance. The long-term concerns with metallic inserts are particularly problematic for use in children due to the necessary longevity of the repaired bone.

Bone grafting also suffers from limitations and downsides. Generally, there are three types of bone grafting—autogenous, allogenic, and xenogenic. Autogenous grafts (often referred to as autografts) employ the patient's own bone removed from another section of their body. Advantages of autogenous bone grafting is that there is substantially little risk of tissue rejection and the tissue contains living cellular material that is beneficial for healing. A significant disadvantage is that it requires an additional surgery and the removal of bone from that site. For some patients, autogenous bone grafting is not a possibility at all. Allogenic bone grafting employs bone tissue removed from a cadaver. Xenogenic bone grafting employs bone tissue removed from another species, e.g., use of a cow's bone tissue in a human patient. Allogenic and xenogeneic bone grafting suffer several problems including difficulties in tissue matching and potential rejection and the lack of living cellular material in the bone itself. Due to the lack of living cellular material in allogenic and xenogenic bone tissue, the grafted bones are unable to grow and merely serve as a framework for other tissue to grow over.

There has been investigation into alternative sources for bone tissue engineering. One such avenue has been the investigation of polymeric scaffolds. However, many polymeric scaffolds have proven unsuitable due to poor mechanical properties such as tensile strength, elastic modulus, compression, the pore size and hierarchy of pores.

Thus, there is a need for alternative bone grafting materials. Further, there is a need for bone grafting materials that have an ability to integrate with adjacent tissue. Additionally, it is desirable to provide bone grafting materials that can employ living cellular material.

BRIEF SUMMARY OF A PREFERRED EMBODIMENT

An advantage of the invention is that it provides compositions and methods of preparing the compositions useful for bone grafts. It is an advantage of the present invention that the compositions are particularly suitable for grafting complex bone defects. Still a further advantage of the present invention is that the compositions have many properties that are desirable for bone grafting materials, including, for example, mechanical properties, desired pore size, and hierarchical pore structure.

In an embodiment, the present invention relates to a scaffold composition comprising a biocompatible polymer and a clay. Preferably, the polymer is a natural polymer, synthetic polymer, blend, combination, or mixture of the same. Preferably, the clay comprises a smectite. Optionally, the scaffold can be coated in an additional ingredient such as amino acid, anesthetic, antibiotic, antiangiogenic agent, antibody, anticoagulant, antineoplastic agent, antiviral agent, biomaterial, bone morphogenetic proteins, carbohydrate, cell, cytotoxic agent, drug, electrolyte, growth factor, immunomodulator, inorganic material, lipid, mineral, oligonucleotide, osteoblast, osteoclast, osteo stem cell, polypeptide, progenitor, protein, therapeutic agent, tissue, tissue or cell aggregate, vasoactive agent, and combinations thereof.

In an embodiment, the present invention relates to a method of preparing a scaffold composition comprising dissolving a biocompatible polymer in a solvent to form a dissolved polymer, adding clay to the dissolved polymer to form a clay and polymer mixture, and freeze drying the clay and polymer mixture to form a scaffold. Preferably, the polymer is a natural polymer, synthetic polymer, blend, combination, or mixture of the same. Preferably, the clay comprises a smectite. Optionally, the method can further comprise coating the scaffold with an additional ingredient such as amino acid, anesthetic, antibiotic, antiangiogenic agent, antibody, anticoagulant, antineoplastic agent, antiviral agent, biomaterial, bone morphogenetic proteins, carbohydrate, cell, cytotoxic agent, drug, electrolyte, growth factor, immunomodulator, inorganic material, lipid, mineral, oligonucleotide, osteoblast, osteoclast, osteo stem cell, polypeptide, progenitor, protein, therapeutic agent, tissue, tissue or cell aggregate, vasoactive agent, and combinations thereof.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

FIG. 2A shows an exemplary scaffold of a preferred embodiment.

FIG. 5A shows an exemplary scaffold block.

FIG. 5B shows exemplary stack of scaffold blocks according to FIG. 5A stacked in an array of 2.

FIG. 5C show an exemplary stack of scaffold blocks according to FIG. 5A stacked in an array of 4.

FIG. 5D show an exemplary stack of scaffold blocks according to FIG. 5A stacked in an array of 8.

Figure 1B:
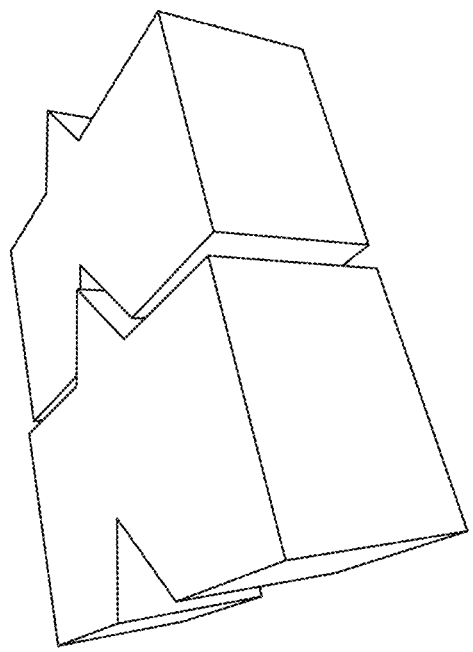
FIG. 1B shows an exemplary preferred geometry of the scaffold blocks.
Figure 1A:
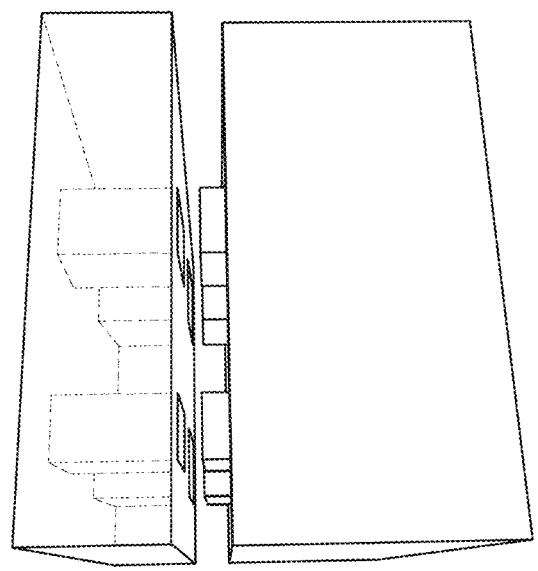
FIG. 1A shows an exemplary preferred geometry of the scaffold blocks.
Figure 1D:
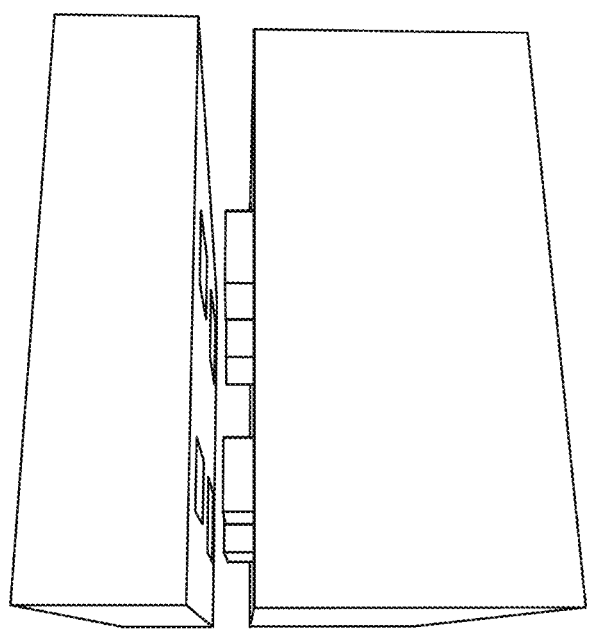
FIG. 1D shows an exemplary preferred geometry of the scaffold blocks.
Figure 1C:
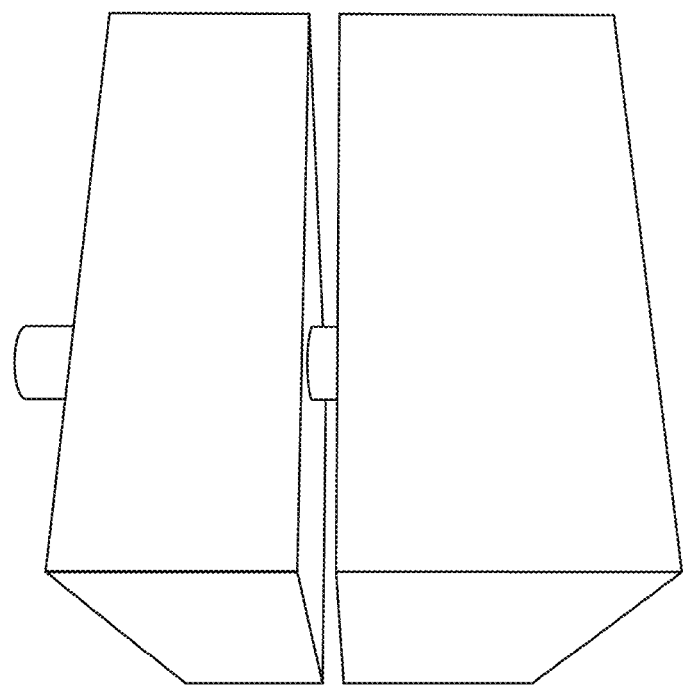
FIG. 1C shows an exemplary preferred geometry of the scaffold blocks.

Various embodiments of the present invention will be described in detail with reference to the figures, wherein like reference numerals represent like parts throughout the several views of various embodiments. Reference to various embodiments does not limit the scope of the invention. Figures represented herein are not limitations to the various embodiments according to the invention and are presented for exemplary illustration of the invention.

DETAILED DESCRIPTION OF THE INVENTION

It is to be understood that all terminology used herein is for the purpose of describing particular embodiments only, and is not intended to be limiting in any manner or scope. For example, as used herein the singular forms "a," "an" and "the" can include plural referents unless the content clearly indicates otherwise. Additionally, all units, prefixes, and symbols may be denoted in its SI accepted form.

Numeric ranges recited within the specification are inclusive of the numbers defining the range and include each integer and fraction within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range, including decimals and fractions. For example, description of a range such as from 1 to 6 should be considered to have specifically disclosed sub-ranges such as from 1 to 3, from 1 to 4.2, from 1 to 5½, from 2 to 4, from 2 to 6, from 3 to 6 etc., as well as individual numbers within that range, for example, 1, 2, 3, 4, 5, and 6. This applies regardless of the breadth of the range.

As used herein, the term "biocompatible" refers to materials that interact with the body without an undesirable affect.

As used herein, the term "biodegradable" refers to materials which can be metabolized by the body, e.g., enzymatically, chemically, or otherwise degrade in vivo.

As used herein, the term "controlled release" refers to control of the rate of release, quantity released, or combination thereof of a drug, therapeutic agent, or combination thereof. A controlled release can be continuous or discontinuous, linear or non-linear.

As used herein, the term "drug" refers to a substance intended for use in the cure, mitigation, prevention, and/or treatment of a disease, disorder, injury, or other condition in a human and/or non-human animal species.

As used herein, the term "oligomer" refers to a molecular complex comprised of between one and ten monomeric units. For example, dimers, trimers, and tetramers, are considered oligomers. Furthermore, unless otherwise specifically limited, the term "oligomer" shall include all possible isomeric configurations of the molecule, including, but are not limited to isotactic, syndiotactic and random symmetries, and combinations thereof. Furthermore, unless otherwise specifically limited, the term "oligomer" shall include all possible geometrical configurations of the molecule.

As used herein, the term "polymer" refers to a molecular complex comprised of more than ten monomeric units and generally includes, but is not limited to, homopolymers, copolymers, such as for example, block, graft, random and alternating copolymers, terpolymers, and higher "x"mers, wherein "x" is between 4 and 100, and further including their analogs, derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

As used herein, the term "sustained release" refers to the continual release of a drug, therapeutic agent, or combination thereof over a period of time.

As used herein, "therapeutic agent" refers to any compound or composition of matter which, when administered to an organism (human or nonhuman animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. The term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthlitics; antiasthmatic agents; anticonvulsants; antidepressants; antihistamines; anti-inflammatory agents; antinauseants; antimigrane agents; antineoplastics; antiprulitics; antipsychotics; antipyretics; antispasmodics; cardiovascular preparations (including calcium channel blockers, 13-blockers, 13-agonists and antiarrythmics); antihypertensives; chemotherapeutics, diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymelic forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like).

As used herein, the term "therapeutic effect" means any improvement in the condition of a subject, human or animal, treated according to the subject method, including obtaining a preventative or prophylactic effect, or any alleviation of the severity of signs and symptoms of a disease, disorder, injury, or other condition which can be detected by means of physical examination, laboratory or instrumental methods.

As used herein, the terms "treat" and "treating" refer to: (i) alleviating the severity of signs and symptoms of a disease, disorder, injury, or other condition; (ii) inhibiting the a disease, disorder, injury, or other condition; and/or (iii) preventing a disease, disorder, injury, or other condition from occurring or recurring in an animal or human that may be predisposed to the disease, disorder and/or other condition.

Scaffolds

The present invention provides scaffolds comprising a clay and a polymer and methods to transform the clay into nanoclay. The scaffold material may also include additional ingredients. The scaffolds can be prepared in small blocks. These blocks are defined as three dimensional elements of a customizable shape and size. The blocks can be prepared in any desired size. Preferably the blocks have porosities with at least one dimension that is at least 200 nanometers, more preferably at least 400 nanometers, and most preferably at least 500 nanometers. In a preferred embodiment the blocks have porosities with at least two dimensions that are at least 200 nanometers, more preferably at least 400 nanometers, and most preferably at least 500 nanometers. In a preferred embodiment the blocks have porosities with three dimensions that are at least 200 nanometers, more preferably at least 400 nanometers, and most preferably at least 500 nanometers. These porosities are verified using scanning electron microscopy imaging or micro tomography x-ray scanning. The purpose of these porosities is to allow for fluid flow, cell growth and tissue regeneration and the pore to solid volume in the scaffold should exceed 80%. Preferably, the blocks have at least one dimension that is less than 50 millimeters, more preferably less than 25 millimeters, and most preferably less than 15 millimeters.

In a preferred embodiment the scaffolds and/or scaffold blocks have at least two dimensions that are between 0.1 millimeters and 50 millimeters, more preferably between 0.5 millimeter and 25 millimeters, and most preferably between 1 millimeter and 15 millimeters. In a preferred embodiment the blocks have three dimensions that are less than less than 50 millimeters, more preferably less than 25 millimeters, and most preferably less than 15 millimeters.

The blocks can be prepared in any desired shape. For example, the blocks can be prepared with straight edges or rounded edges. The blocks can be in the shape of a sphere, a cube, or any polygon. In the case of a polygon, the polygon can have any of its sides straight or rounded.

Figure 2B:
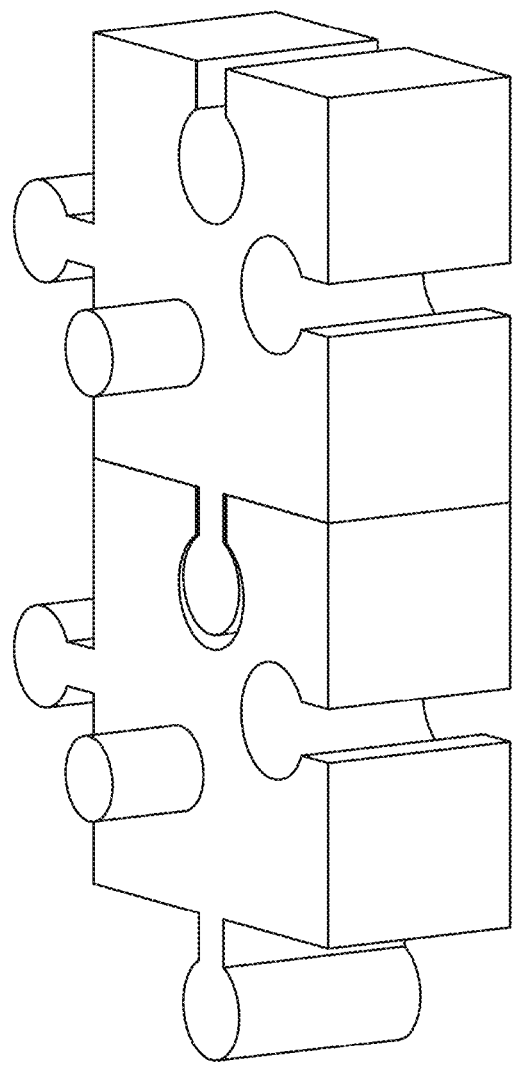
FIG. 2B shows two scaffold blocks of FIG. 2A interconnected in a preferred embodiment.
Figure 2C:
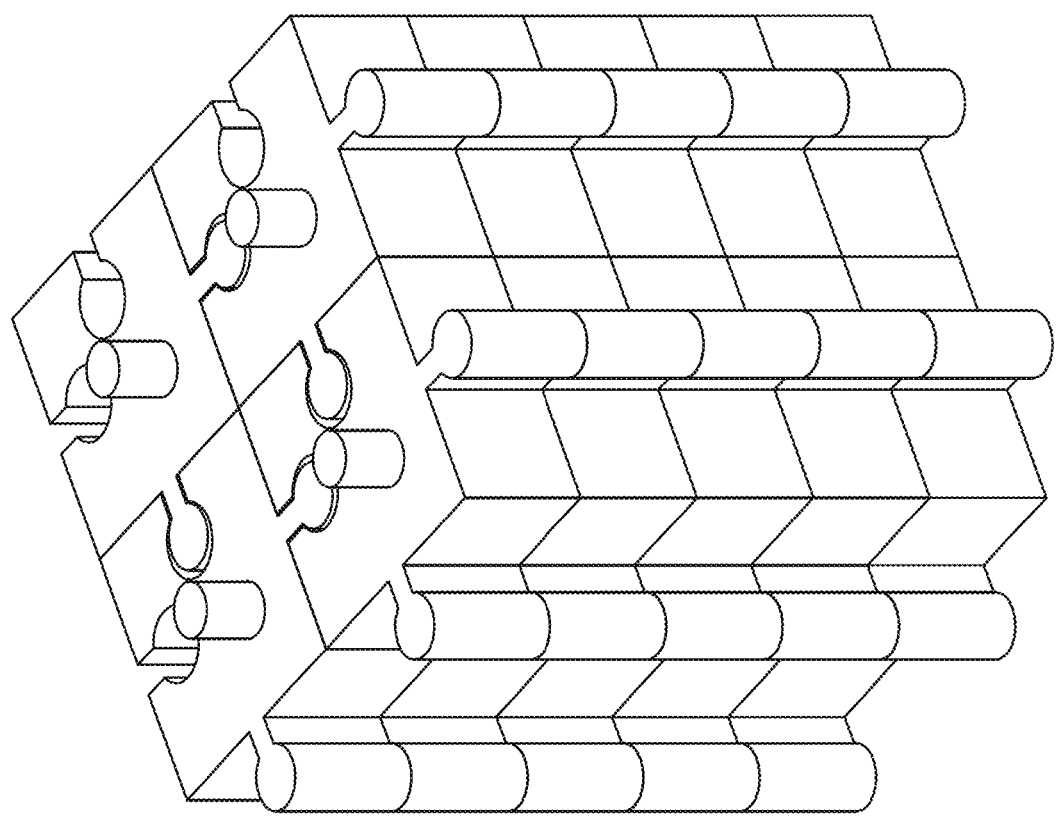
FIG. 2C shows twenty scaffold blocks of FIG. 2A interconnected in a preferred embodiment.

A defect site of an injured bone can be filled with a scaffold comprising one or more blocks. In embodiments of the composition including more than one scaffold block, the scaffold blocks can be interconnected through geometrical interlocking, stacking, adhesion, or in any other suitable manner. FIGS. 1A-D and 2A-C show non-limiting examples of possible geometries for the scaffold blocks and configurations for connecting scaffolds into blocks. The scaffold blocks can be prepared in a desired shape through fabrication or by cutting. The bridging between blocks would be necessary for filling large nonunion bone defects. FIGS. 2A-2C provide non-limiting example of an effective shape/size block that may be used. An advantage of this design is that the same identical block may be used for a large defect and multiple types of blocks are not needed which would reduce complexity of on location assembly of block for a patient. These blocks can be made of scaffold materials as described herein. Advantageously, the shape of scaffold blocks can be selected to fit optimally with the bone defects.

The scaffolds and scaffold blocks can also contain any number of optional ingredients added for certain desired properties and/or effects.

The scaffolds and scaffold blocks can be sterilized. The scaffolds can facilitate or assist the generation of bone tissue, provide hierarchical structure for tissue to regenerate on, provide a vehicle for the delivery of various optional ingredients. The scaffolds can allow for the use of the patient's own cells (autologous treatment) for bone regeneration. The generation of bone tissue on, over, and/or around the scaffolds can be seen based on the formation of an extracellular matrix and by seeing calcium formation.

Clay

The scaffolds include a clay. As used herein, the clay is sometimes referred to as a nanoclay due to properties of the clay that are measured on the nanoscale. Suitable clays for forming the scaffolds can include, but are not limited to smectite group of clay minerals such as, bentonite, beidellite, hectorite, nontronite, saponite, and combinations thereof. Reference to different species of clays includes the various types of that species, e.g., bentonite encompasses sodium bentonite, calcium bentonite, and potassium bentonite. Preferred bentonite clay includes sodium bentonite, calcium bentonite, and potassium bentonite. Preferred montmorillonite clay includes sodium montmorillonite and calcium montmorillonite and montmorillonite with other cations. In embodiments employing more than one clay, the multiple clays can be in a mixture or as separate clays.

The clay can comprise between 0.5 wt. % to 99.5 wt. % of the scaffold or scaffold block. Preferably, the clay can comprise between 1 wt. % to 80 wt. % of the scaffold or scaffold block. More preferably, the clay can comprise between 5 wt. % to 75 wt. % of the scaffold or scaffold block. In a preferred embodiment, the scaffolds have between 1 wt. % and about 20 wt. % clay, more preferably between about 2 and 15 wt. %, most preferably between about 5 wt. % and about 20 wt. %.

Polymer

The scaffolds include a polymer. The compositions can include more than one polymer. Preferably the polymer is biocompatible. In some embodiments of the invention, the polymer can be biodegradable and/or conductive.

Suitable polymers for use in the scaffolds include any polymeric material without limitation so long as it possess the necessary biocompatible and/or biodegradable properties. Preferred polymers include those of natural and synthetic origins, and blends, combinations, or mixtures of the same, which can be formed into copolymers, terpolymers, or "x" mers.

Examples of natural polymers include, but are not limited to, proteins and polysaccharides, which can be used individually, in blends, combinations and/or mixtures, Preferred natural polymers, include, but are not limited to, albumin, alginate, cellulose (which is inclusive of regenerated cellulose), chitin, chitosan, collagen, gelatin, heparin, and other naturally occurring polymers such as regenerated silk or polysaccharide, and/or blends, combinations, or mixtures of the same.

Examples of synthetic polymers include, but are not limited to, poly(amino acids), polyanhydrides, polyesters, poly(alpha-hydroxy acids), poly(lactones), poly(orthocarbonates), poly(orthoesters), poly(phosphoesters), or polyphosphazenes, which can be used individually, in blends, combinations and/or mixtures. Preferred synthetic polymers, include, but are not limited to, polycaprolactone (PCL), poly(delta-valerolactone), poly(1,5-dioxepan-2-one), poly (epsilon-aprolactone), poly(ester urethane) (PEU), polygalactouronic acid, poly(gamma-butyrolactone), polyglycolic acid, poly(alpha-hydroxy acids), polyhydroxyalkanoate (PHA), polyhydroxybutyric acid, poly(3-hydroxybutyrate-co-3-hydroxyvalerate (PHBV), polylactic acid (PLA) (e.g., poly(DL-lactic acid) and poly(L-lactic acid)), copolymers of lactic acid-glycolic acid such as poly(lactic-co-glycolic acid) (PLGA), poly(lactic acid-co-caprolactone) (PLCL), poly(trimethylene carbonate), poly-8-valerolactone, or blends, combinations, and mixtures of the same.

Examples of conductive polymers include, but are not limited to, polyacrylonitrile, polyimide, and regenerated cellulose. In an aspect of the invention, the polymer, scaffold, and/or scaffold black can be coated with a conductive material. In an aspect of the invention, conductive polymers may be preferred for in situ sensor applications and for evaluation of degradation.

In an embodiment of the invention, preferred polymers include, but are not limited to, chitosan-polygalactouronic acid and polycaprolactone.

The polymer can comprise between 1 wt. % to 99.5 wt. % of the scaffold or scaffold block. Preferably, the polymer can comprise between 25 wt. % to 95 wt. % of the scaffold or scaffold block. More preferably, the polymer can comprise between 50 wt. % to 90 wt. % of the scaffold or scaffold block.

Additional Ingredients

The scaffolds and scaffold blocks can optionally contain any number of additional ingredients added for certain desired properties and/or effects. The additional ingredients can be naturally occurring or synthetic, organic or inorganic. Suitable additional ingredients, include, but are not limited to amino acids, anesthetics, antibiotics, antiangiogenic agents, antibodies, anticoagulants, antineoplastic agents, antiviral agents, biomaterials, bone morphogenetic proteins, carbohydrates, cells, cytotoxic agents, drugs, electrolytes, growth factors, immunomodulators, inorganic materials, lipids, minerals (such as hydroxyapatite mineral (HAP)), oligonucleotides, osteoblasts, osteoclasts, osteo stem cells, polypeptides, progenitors, proteins, stem cells (adult and/or embryonic), therapeutic agents, tissues, tissue or cell aggregates, vasoactive agents, and combinations thereof. Preferred proteins include bone morphogenetic protein (BMP), particularly BMP-2 and BMP-7.

It has been found that increased backbone length of amino acids can increase molecular interaction between polymer, amino acid and clay allowing for significant improvement in the mechanical property. Unnatural amino acids provide longer backbone chains and are thus candidates as modifiers. Thus, in some embodiments of the invention, it is preferable to have an amino acid with a carbon backbone chain length of at least five carbon atoms. Preferred amino acids have a carbon chain length of between one and about ten. In some embodiments, preferred amino acids include but are not limited to, aminovaleric, amino caprylic, amino pimelic acids and combinations thereof.

The additional ingredients can be selected to impart particular functionalities or properties. For example, additional ingredients can be selected to affect and/or control the mechanical, biological and degradation properties of the scaffold. In another aspect of the invention, specific additional ingredients can be selected for the desired properties or effects and based on the patient. For example, in the case of a human patient, a human osteoblast can be used, whereas if the patient is a cow a bovine osteoblast can be used. Similarly, certain additional ingredients can be specifically tailored to the patient based on use of their own genetic and/or cellular materials, e.g., cell lines developed based on compatibility or directly from the patient's own genetic and/or cellular materials. In a preferred embodiment of the invention, the scaffolds and/or scaffold blocks can incorporate autologous treatments.

Any suitable amount of additional ingredients can be used in the scaffolds and scaffold blocks. The appropriate amount of an additional ingredient can be dictated by the patient's condition, age, size, general health, medical conditions, allergies, etc. Generally, the additional ingredients will be included in an amount of between 0.01 wt. % and 50 wt. % of the composition. The additional ingredients can be part of the scaffolds and/or scaffold blocks, impregnated within the scaffolds and/or scaffold blocks, coat the scaffolds or scaffold blocks, or any combination thereof. The additional ingredients can be attached to, coat, and/or modify the clay or polymer. In an aspect of the invention, when used to coat the scaffolds, the additional ingredients can be prepared in a solution and the scaffolds can be soaked in the solution.

Methods of Preparing the Scaffolds and Scaffold Blocks

A freeze-drying method can be used to prepare the scaffolds. In such a method, the polymer is first dissolved in a solvent followed by slowly adding the clay. In a preferred embodiment, the clay can be modified by one or more of the additional ingredients as described above. Any suitable method for modifying the clay can be used. After adding the clay to the dissolved polymer, another solvent can be added to the resultant followed by controlled freeze drying.

Any suitable solvent can be used to dissolve the polymer and the solvent can be selected based on the polymer to be dissolved. Similarly, any suitable solvent can be used for the freeze-drying step. Preferred solvents for the freeze-drying step include those having a melting point that is below that of the scaffold components. An exemplary alcohol useful for freeze drying is isopropyl alcohol.

Figure 3:
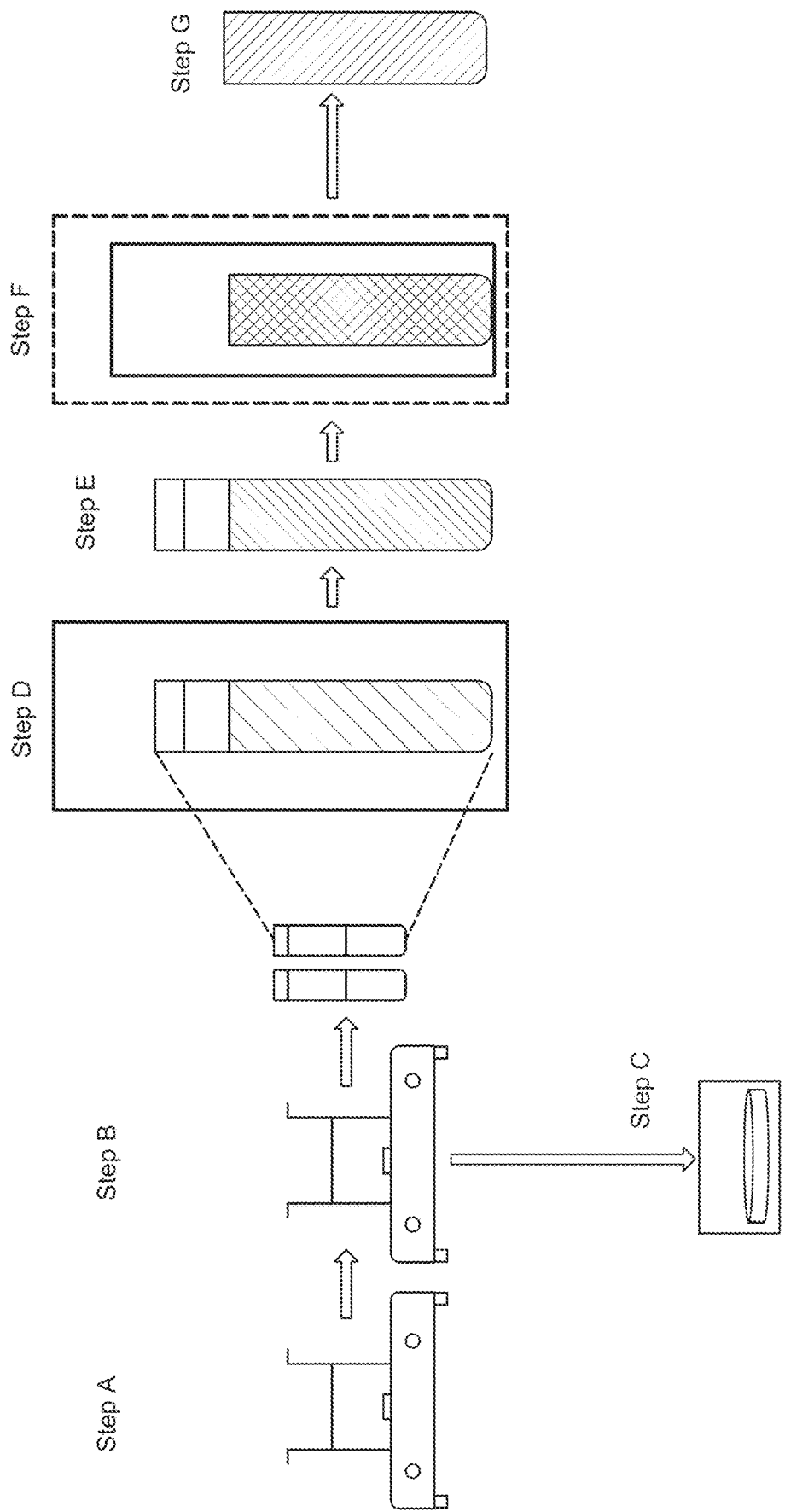
FIG. 3 shows a process diagram of a preferred method of preparing nanoclay composite films and scaffolds.

FIG. 3 provides an exemplary method for preparing scaffolds according to a preferred embodiment of the invention. For example purposes, FIG. 3 shows a polymer solution can be prepared (Step A) and a clay can be added (Step B). Preferably, the mixture of clay and polymer can be centrifuged. In a preferred embodiment, the mixture of polymer and clay is allowed to dry to form a film before centrifuging (Optional Step C). Next a polymer composite solution (solution of polymer and clay) can be cooled to freeze (Step D). A solvent, such as an alcohol, can be added during the freezing step. The solvent should be allowed to freeze into crystals (Step E). The composite with frozen solvent can then be immersed in an extraction solvent (for example, another alcohol, preferably ethanol) so that the solvent crystals can be extracted (Step F). Preferably the extraction solvent is replaced at regular intervals (e.g., daily, every 12 hours, etc.). Finally, the porous composite structure, now a scaffold, is removed and dried under laboratory conditions (Step G). This scaffold can now be cut and prepared in a desired shape. In another embodiment of the invention, the freezing steps can be performed in a mold of the desired shape and dimensions. Additional ingredients can be added prior to the freezing step or after the scaffold is removed. For example, if certain additional ingredients are desired to be part of the scaffold, they can be added prior to the freezing step. However, in other embodiments, it may be preferred to add the additional ingredients after the scaffold is prepared, e.g., when seeding a scaffold with cells.

Composite scaffolds containing in situ HAPclay at a desired concentration concentration and PCL can be prepared as described in FIG. 3. Suitable concentrations of the clay can be as set forth above. Cylindrical shaped frozen samples of the composite solution can be carefully removed from polypropylene (PP) centrifuge tubes and further immersed in absolute ethanol (cooled to −20° C.) for solvent extraction. The cylindrical shaped porous samples, known as scaffolds, were removed and dried at room temperature.

Some of the optional ingredients can be prepared in a "biomimetic" manner in situ. For example, precursors to the desired optional ingredient can be added to the space between the clay sheets on the nanoscale so that an optional ingredient is formed between the sheets of clay. For example, amino acid molecules can be attached to the clay sheets to create HAP in a manner similar to the way HAP is naturally made in bones. This "biomimetic" in situ HAPclay is morphologically and crystallographically identical to the natural HAP found in bones, while made in a synthetically engineered manner.

Methods of Using the Scaffolds and Scaffold Blocks

Individual scaffolds and/or scaffold blocks can be prepared and/or selected based on size and shape. They can be combined to fit a bone defect or injury. Suitable optional ingredients can be added to the scaffolds and/or scaffold blocks. The scaffolds and scaffold blocks can be added to a bone injury or defect through the appropriate medical treatment such as traditional surgery or minimally invasive surgery (e.g., arthroscopic or laparoscopic).

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following Examples are provided herein:

Sodium montmorillonite clay (Na-MMT clay) was obtained from Clay Minerals Respiratory at the University of Missouri, Columbia.

The polymer polycaprolactone (PCL) was obtained from Sigma-Aldrich.

The amino acid 5-aminovaleric acid was obtained from Sigma-Aldrich. 1,4-dioxane was obtained from Sigma-Aldrich.

$Na_2HPO_4$ and $CaCl_2$) were obtained from J. T. Baker.

Example 1

Preparation of an Exemplary Scaffold

The preparation procedure of PCL/in situ HAPclay 3D scaffolds is described in detail in our previous studies[1,2]. Briefly, sodium montmorillonite clay (Na-MMT) was initially modified with 5-aminovaleric acid, as described in previous studies. A novel biomineralization procedure was used to grow hydroxyapatite inside clay galleries using the amino acids, thus making in situ, HAPclay[3-5]. Further, 3D PCL scaffolds were prepared with 10 wt % in situ HAPclay. For this, PCL solution was prepared by dissolving 3.6 grams of the polymer in 40 ml of 1,4 dioxane. Sonicated suspension of in situ HAPclay was prepared by adding 4 grams of in situ HAPclay into 16 ml dioxane which was then added to the polymer solution and then stirred for two hours. Freeze extraction method was used to obtain 30 scaffolds from this solution.

Cell Line and Culture Medium

Human osteoblast cell line (hFOB 1.19) were purchased from ATCC and maintained in a media consisting of 90% HyQ Dulbecco's Modified Eagle medium (DMEM-12 (1:1)) from Hyclone, 10% FBS from ATCC and 0.6% G418 solution (antibiotic) from JR scientific. All the cells were maintained at 37° C. and 5% $CO_2$ in completely humidified incubator. Cell culture media were changed every 3 days.

Preparation of Bone Graft Blocks

Figure 4A:
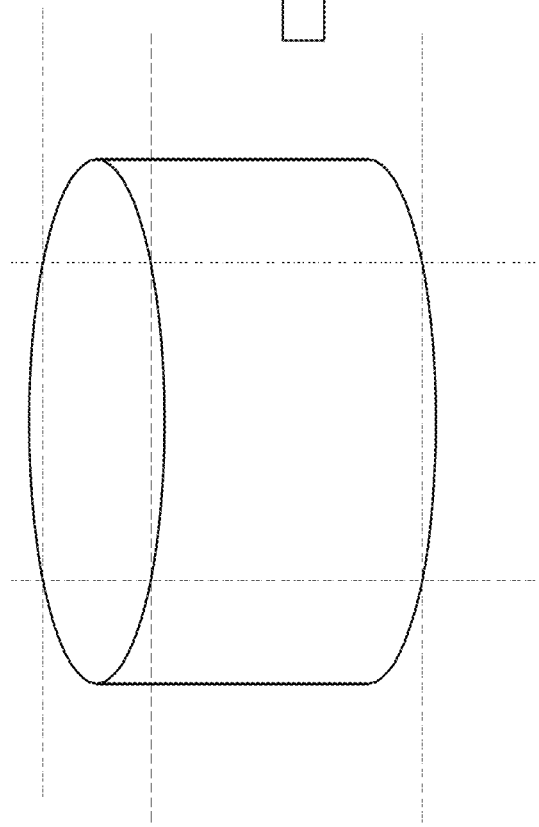
FIG. 4A shows an exemplary representation of a how a scaffold block can be prepared to desired dimension.
Figure 4B:
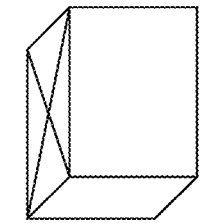
FIG. 4B shows an exemplary representation of how multiple scaffold blocks can be arranged with respect to each other.
Figure 4B:
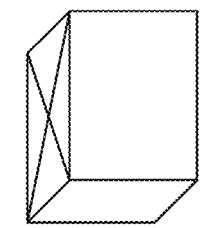
Figure 4B:
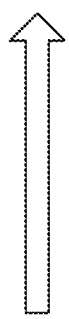
Figure 4B:
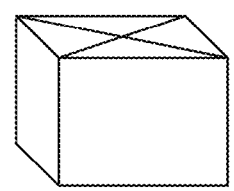
Figure 4B:
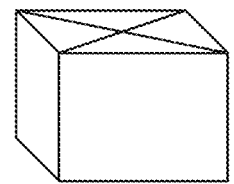
Figure 4C:
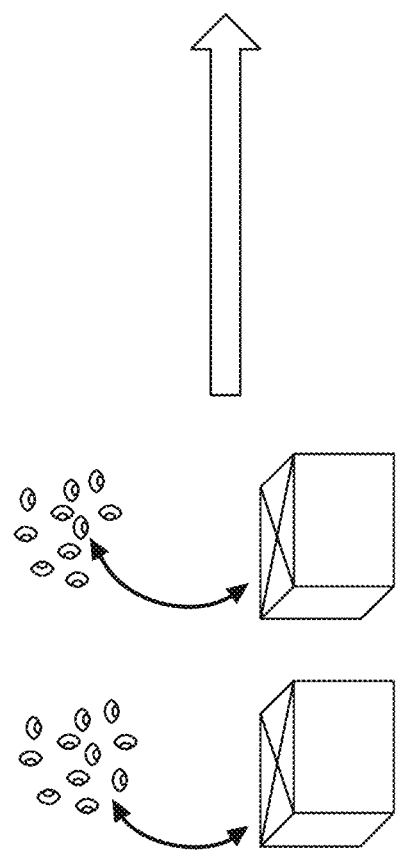
FIG. 4C shows an exemplary cell-seeding and preparation of cell-seeded scaffold block sandwich.

FIGS. 4A-C show an exemplary representation of how a scaffold can be prepared in a desired shape and dimension and seeded. Specifically, FIG. 4A shows an example of how PCL/HAPclay scaffolds were cut into rectangular shapes in dimension of 6 mm×4 mm×4 mm. Those scaffolds were decontaminated under UV light for 45 minutes. The scaffolds were kept under 70% alcohol overnight followed by washing with PBS. The scaffolds were placed on a non-treated 96-wellplate (each block on a separate well) and kept immersed in seeding culture media overnight. Note the schematic representation in FIGS. 4A-C is not to scale and not intended to be limiting, but is an exemplary process used in evaluating the invention.

Bone Morphogenetic Protein (BMP-2) Loading and Cell Seeding on Scaffolds

Small sections of scaffold blocks cut into 4 mm×4 mm×6 mm pieces were kept under ultra violet light for 45 minutes. The samples were immersed in 100% ethanol for 24 hours for sterilization after which the samples were washed with PBS. A solution of BMP 2 (from Genscript Cat. No. Z02913-50) was prepared by dissolving 13 μg in 100 ml cell culture grade water. Sterilized samples were immersed into the freshly prepared BMP 2 solution for 24 hours. After 24 hours, BMP 2 coated samples were kept in the cell culture media for 24 hours prior to using them for cell culture experiments. Initially, $5 \times 10^4$ cells were seeded on each scaffold. On the second day, scaffold blocks were prepared by placing one scaffold on top of another scaffold. Uncoated scaffolds were used as the control throughout the experiment.

Scraping Experiments of Newly Formed ECM

As shown in FIGS. 5A-D, the scaffold blocks were stacked in arrays of 2, 4 and 8. Using a cell scraper, we remove newly formed ECM after separating the blocks and smear on a $CaF_2$ disk for FTIR analysis. Specifically, this test enables the evaluation of beginnings of mineralization and ECM formation at the block interface.

WST-1 Assays

A WST-1 (Roche, Indianapolis) assay was used to perform cell viability analysis following the manufacturer's protocol. In brief, cells were cultured on scaffolds for 48 hours and then the cell-seeded scaffolds were removed from the culture medium, washed with PBS and then placed in a new 96-well plate with a solution consisting of 90 μl of DMEM-12(1:1) medium and 10 μl WST-1 reagent per well and then incubated for 1.5 hours in a standard humidified condition. For scaffold block sandwiches, after 24 hours of cell seeding, sandwiches were made and then those were maintained in culture medium for another 24 hours before doing the assay. The slightly red color solution turned into yellow as metabolically active cells cleave the tetrazolium salts of WST-1 reagent to formazan. Then scaffolds were removed from the 96-well plates and the intensity of yellow color, which directly represents the number of live cells, was read at 450 nm using a microplate spectrophotometer (Bio-Rad, Benchmark Plus). A control was prepared by mixing 10 μl of WST-1 reagent with 90 μl of DMEM-12(1:1) medium in each well of 96-wellplate. The same number of cells were seeded into empty wells which showed no viability (indicated by 'Wellplate' in the graph) because the bottoms of the well-plate are non-treated.

Figure 6:
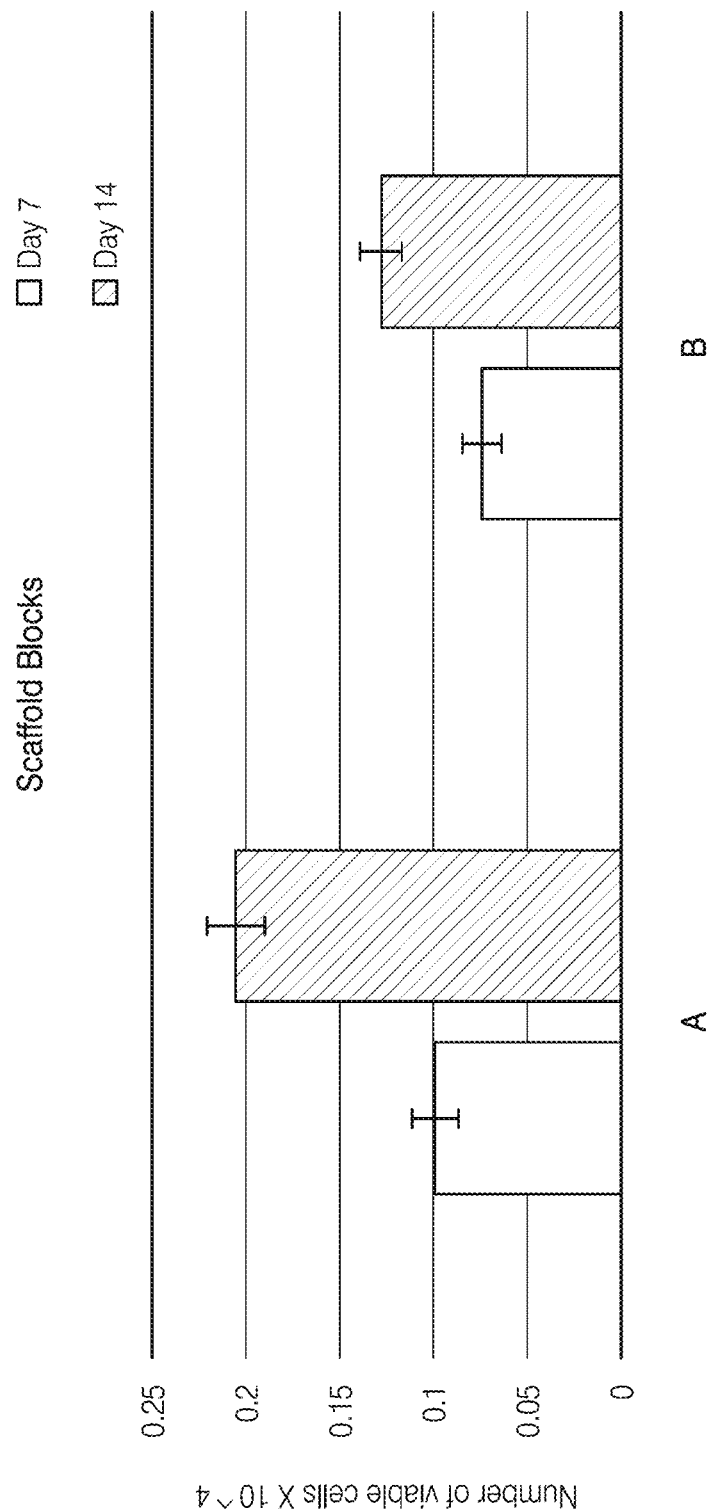
FIG. 6 shows a bar graph representation of the WST-1 assay data for the scaffold blocks coated with seeds, where group A is the number of viable cells at 7 days and 14 days treated with BMP-2 and group B is the number of viable cells at 7 days and 14 days not treated with BMP-2.
Figure 7:
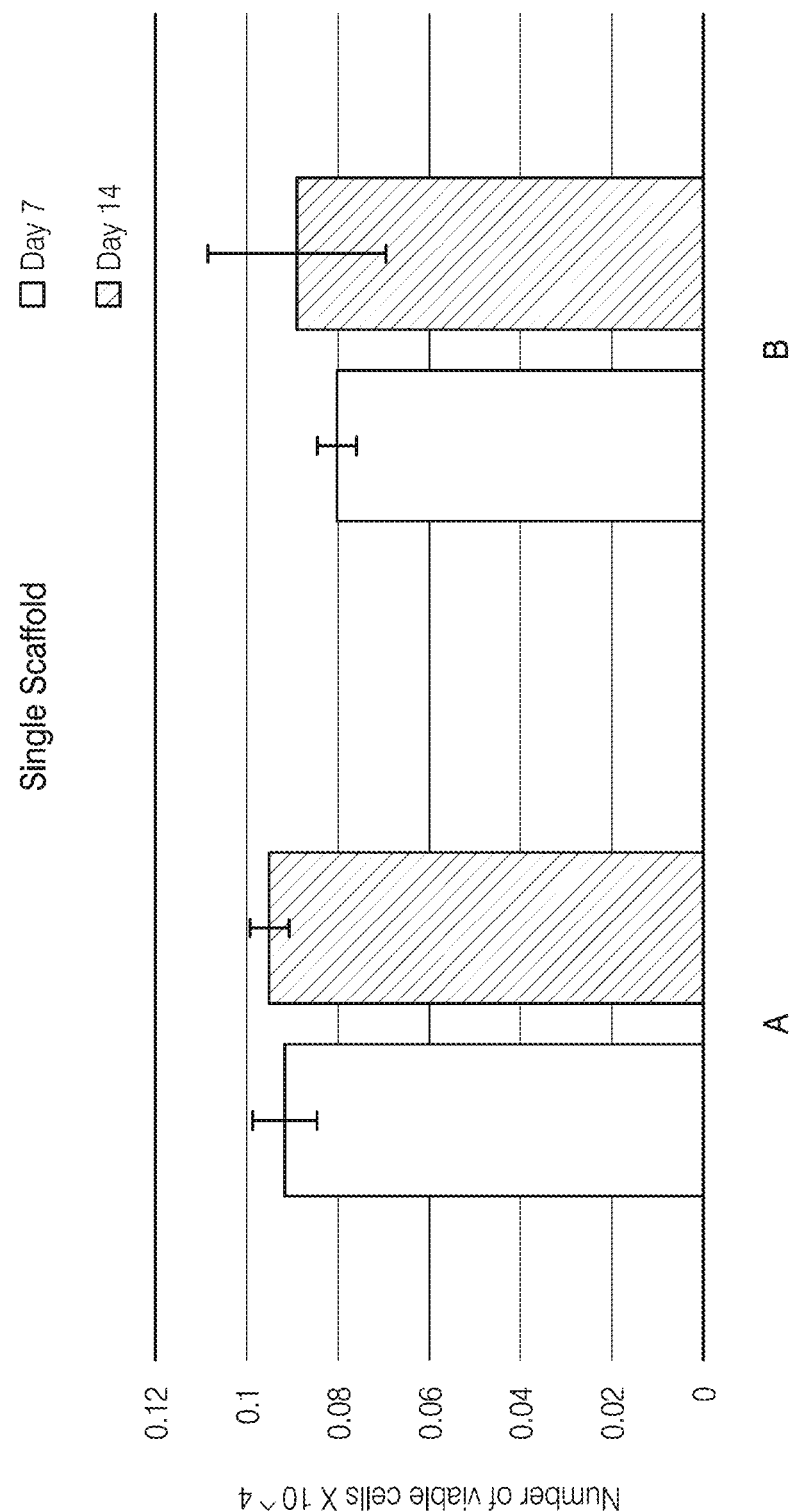
FIG. 7 shows a bar graph representation of the WST-1 assay data for single scaffolds coated with seeds, where group A is the number of viable cells at 7 days and 14 days treated with BMP-2 and group B is the number of viable cells at 7 days and 14 days not treated with BMP-2.

The data from the WST-1 assay is shown in FIGS. 6 and 7. FIG. 6 shows the WST-1 assay data for the scaffold block samples. FIG. 7 shows the WST-1 assay data for the single scaffolds. In both FIGS. 6 and 7, the group of A columns show the number of viable cells coated with BMP-2 and the group of B columns show the number of viable cells not coated with BMP-2. The solid columns are after seven days and the hatched columns are after fourteen days. The data is consistent that the scaffold blocks and single scaffolds both showed higher cell viability for those scaffold compositions that were treated with BMP-2.

Alizarin Staining of the BMP2+BMP 7 Together on Scaffolds.

Figure 8A:
FIG. 8A shows an Alizarin red stained single scaffold cell-seeded and uncoated.
Figure 8B:
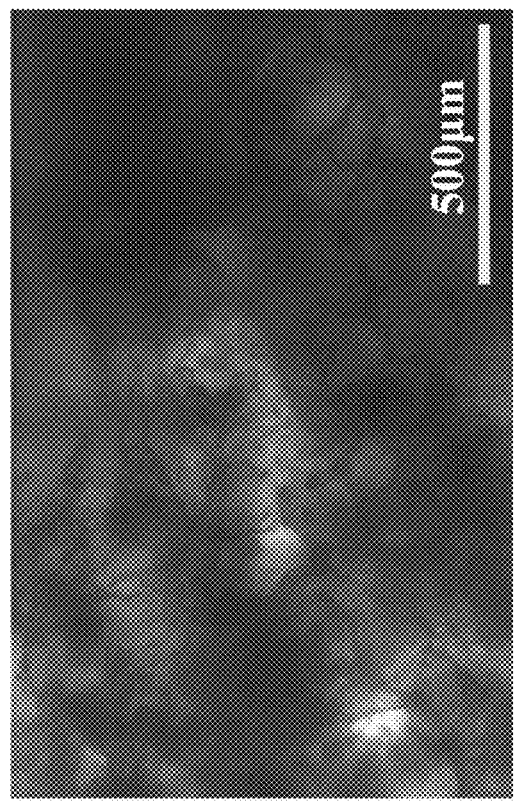
FIG. 8B shows an Alizarin red stained block scaffold cell-seeded and coated with BMP-2.
Figure 8D:
FIG. 8D shows an Alizarin red stained single scaffold cell-seeded and coated with a 50:50 ratio of BMP-2 and BMP-7.
Figure 8C:
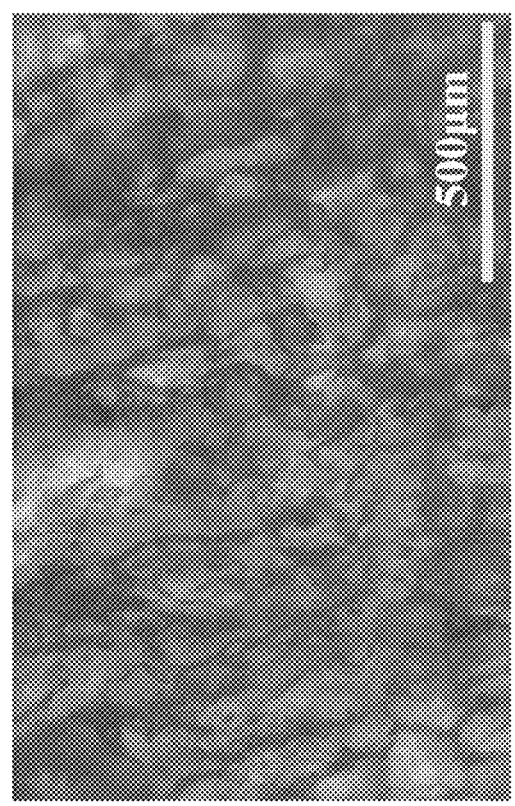
FIG. 8C shows an Alizarin red stained block scaffold cell-seeded and coated with BMP-7.

Alizarin Red S, an anthraquinone derivative, is commonly used to identify calcium in tissue sections. Calcium forms an Alizarin Red S-calcium complex in a chelation process, and the end product is birefringent. The reaction is not strictly specific for calcium. Magnesium, barium, strontium, manganese, and iron can also give signals. These elements are often not present in sufficient concentration to interfere with the staining. Cell seeded scaffolds were washed with PBS afterward and fixed with 2.5% glutaraldehyde overnight. Fixed samples were then washed with PBS and then stained with Alizarin Red S dye (2 grams/100 ml deionized water, pH=4.10-4.15). Further, the samples were washed with cell culture grade water to remove excess dye. Images were then captured using a phase contrast/inverted microscope (Axiovert 40, Zeiss). These images are provided in FIGS. 8A-D where the light spots reflect calcium formation, which indicates bone growth. FIG. 8A shows a single scaffold block uncoated. FIG. 8B shows a block scaffold coated with BMP-2. FIG. 8C shows a block scaffold coated with BMP-7. FIG. 8D shows a single scaffold coated with a 50:50 ratio of BMP-2 and BMP-7. As seen in FIGS. 8A-D, scaffolds coated with BMP-2 and/or BMP-7 show higher calcium formation (indicated in the red regions, which appear light in greyscale) than the scaffold that was not coated (which appear darker). Furthermore, the two scaffold blocks (FIGS. 8B and 8C).

Microscopic Analysis

Figure 9B:
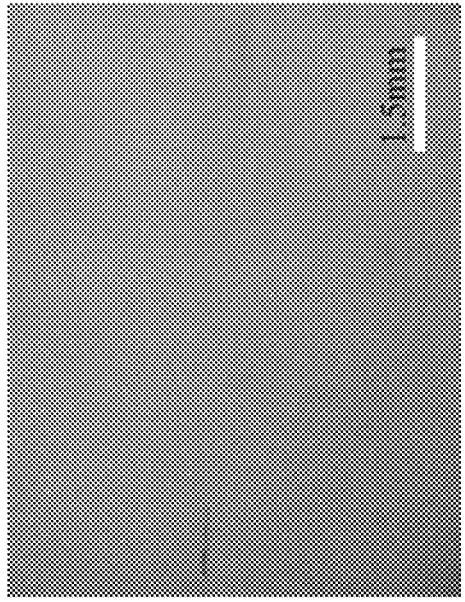
FIG. 9B shows a light microscopy image of the attachments of a block scaffold coated with BMP-2 by the formation of an extracellular matrix.
Figure 9D:
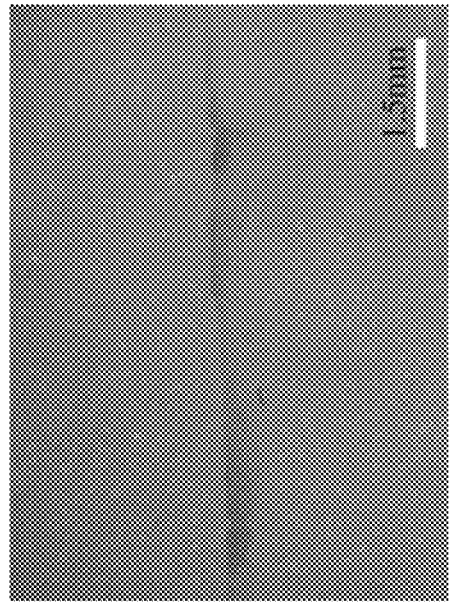
FIG. 9D shows a light microscopy image of the attachments of a block scaffold uncoated by the formation of an extracellular matrix.
Figure 9A:
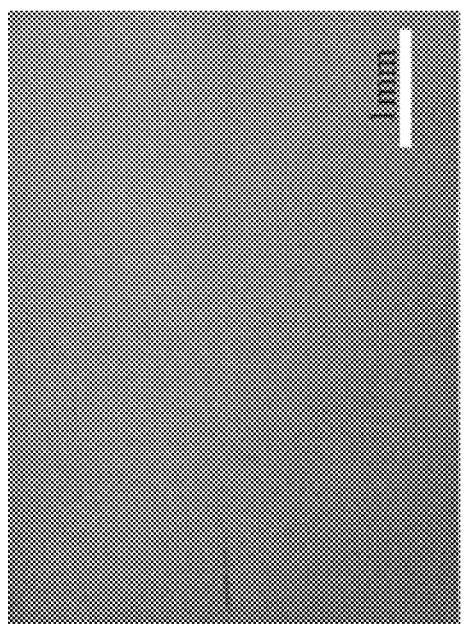
FIG. 9A shows a light microscopy image of the attachments of a single scaffold coated with BMP-2 by the formation of an extracellular matrix.
Figure 9C:
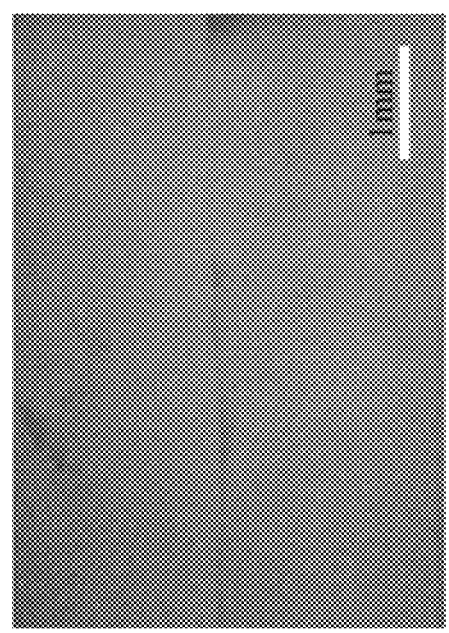
FIG. 9C shows a light microscopy image of the attachments of a single scaffold uncoated by the formation of an extracellular matrix.

A CARV confocal scanning unit attached to Nikon Eclipse E600W fluorescence light microscope was used to obtain images of the bone graft scaffolds blocks. Those images are shown in FIGS. 9A-D. FIGS. 9A and 9B show scaffolds, single and block respectively, coated with BMP-2. FIGS. 9C and 9D show scaffolds, single and block respectively, that were not coated with BMP-2. As seen, the images indicate scaffolds attachment through ECM formation to be weaker in scaffold block without BMP-2 (9C and 9D) than scaffold blocks with BMP-2 (9A and 9B).

Example 1 demonstrates that scaffolds sectioned into blocks have the ability to form an extracellular matrix. Example 1 also demonstrates the ability adhere sectioned scaffold blocks. Additionally, blocks coated with BMP-2 demonstrate improved extracellular matrix formation, mineralization, and adhesion between the scaffold blocks. Nanoclay polycaprolactone blocks with biomineralized hydroxyapatite that are cut into sections and coated with BMP-2 can thus be effectively used for filling large bone defects. The arrangement and organizations of the blocks can be customized easily for bone defect geometry using standard sized blocks.

Example 2

Composite scaffolds containing PCL and 10 wt. % and 20 wt. % in situ HAPclay were prepared as described in FIG. 3. The clay used was sodium montmorillonite clay (Na-MMT). The clay was initially modified with 5-aminovaleric acid. The biomineralization procedure was used to grow hydroxyapatite inside clay galleries using the amino acids, thus making in situ, HAPclay. Cylindrical shaped frozen samples of the composite solution were then carefully removed from polypropylene (PP) centrifuge tubes and further immersed in absolute ethanol (cooled to −20° C.) for solvent extraction. The cylindrical shaped porous samples, known as scaffolds, were removed and dried at room temperature.

The wells containing the PCL composite scaffolds having 10 wt. % in situ HAPclay, were each seeded with $4.77 \times 10^4$ human adult stem cells (MSCs). The wells containing the PCL composite scaffolds having 20 wt. % in situ HAPclay were seeded with $4 \times 10^4$ human MSCs and assayed separately. The MSC seeded scaffold samples were incubated at 37° C., 5% $CO_2$ under humidified conditions for 0 to 41 days. The samples were used for Optical Microscopy imaging, SEM imaging, conducting MTT assays, and ALP assays (assay measuring differentiation capabilities) to evaluate bone formation. The behavior of human MSCs on these scaffolds and films was studied using SEM, atomic force microscopy, and phase contrast microscopy, respectively.

Figures 10A, 10B, 10C:
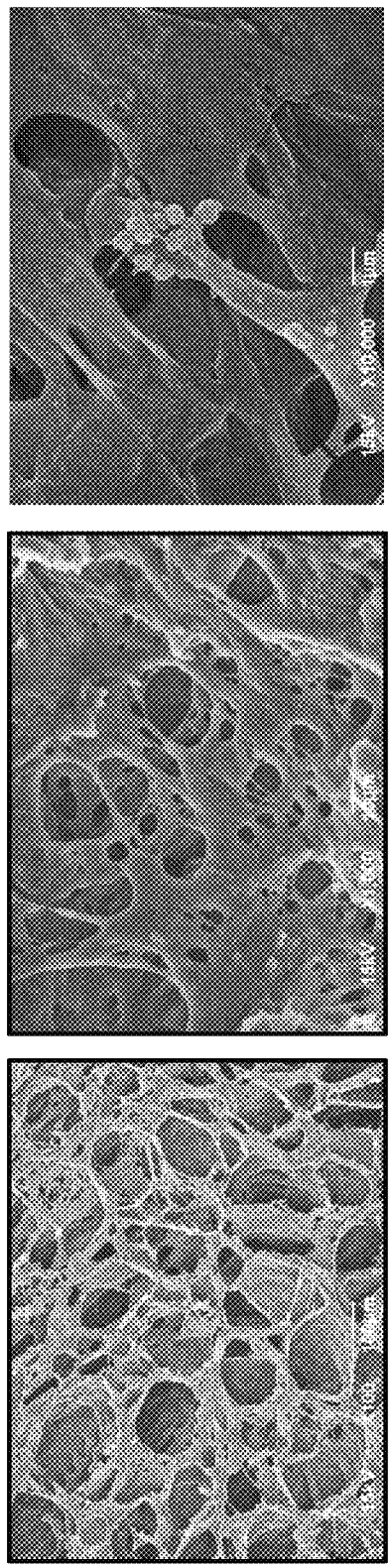
FIG. 10A shows a scanning electron microscope micrograph of a seeded scaffold at 100 times magnification.
FIG. 10B shows a scanning electron microscope micrograph of a seeded scaffold at 1,000 times magnification.
FIG. 10C shows a scanning electron microscope micrograph of a seeded scaffold at 10,000 times magnification.

The MTT and ALP assays demonstrated that cells proliferated and differentiated on the scaffolds. Extensive extracellular matrix development was observed in the middle of the scaffold. Scanning electron microscope (SEM) micrographs were taken of scaffolds with 10 wt. % in situ HAPclay at varying magnification. These SEM micrographs are shown in FIGS. 10A-C. FIG. 10A, taken at 100 times magnification, shows hierarchical structure and interconnected porosity. FIG. 10B, taken at 1,000 times magnification, shows wall microporosity further demonstrating the hierarchical structure of the porosity. This microporosity is essential for ion transportation for adhered cells. FIG. 10C, taken at 10,000 times magnification, shows cells growing on the scaffold demonstrating vesicular delivery and that human MSCs were able to adhere to the scaffolds.

Figure 11B:
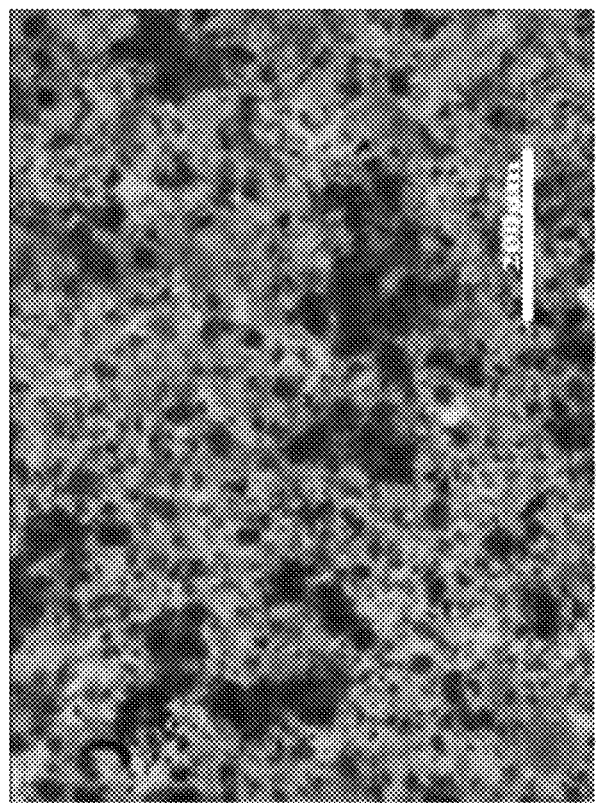
FIG. 11B shows a phase contrast image of Alizarin Red S stained PCL/in situ HAPclay (10 wt %) films seeded with human MSCs after Alizarin Red S staining indicating mineralized extracellular matrix (ECM) formation.
Figure 11A:
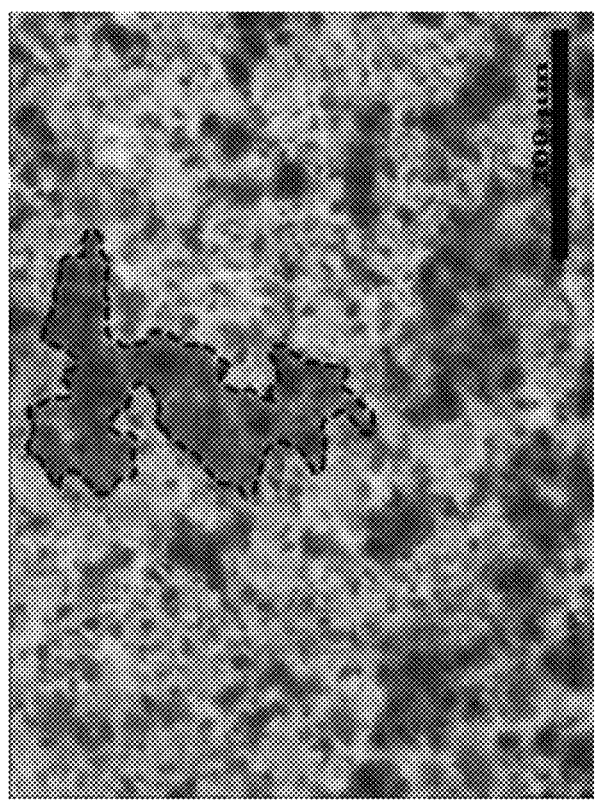
FIG. 11A shows a phase contrast image of Alizarin Red S stained PCL/in situ HAPclay (10 wt %) films seeded with human MSCs after Alizarin Red S staining indicating mineralized extracellular matrix (ECM) formation.
Figure 12A:
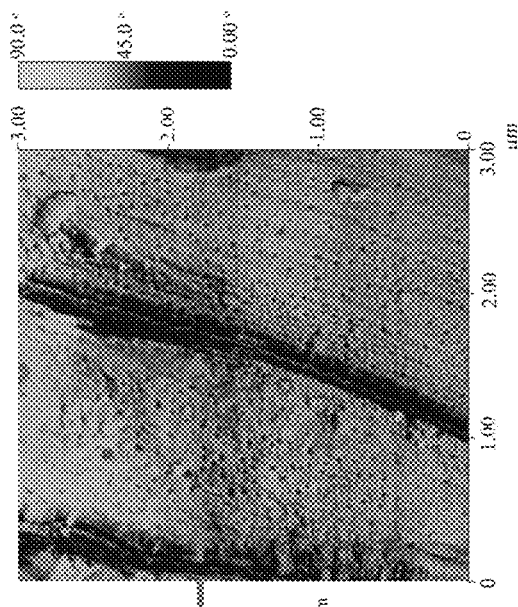
FIG. 12A is an AFM 3D height image/surface plot showing sub-micron scale structure of mineralized ECM formed by MSCs on PCL/in situ HAPclay (10 wt. %) film where the dotted black arrows indicate the formation of collagen fibril bundles.
Figure 12B:
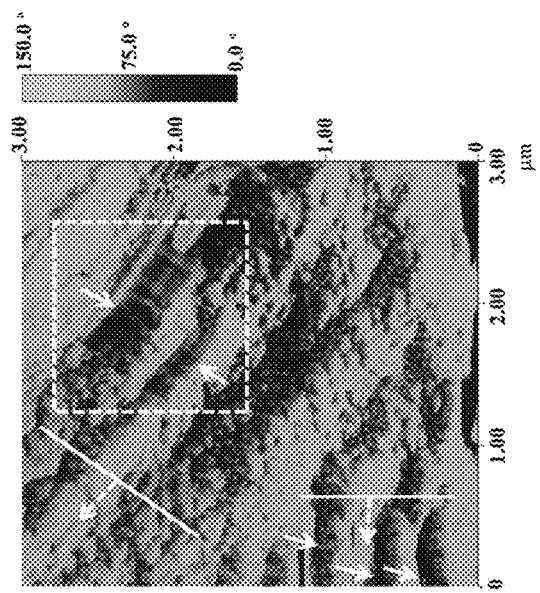
FIG. 12B is a phase image of a region of the AFM 3D height image/surface plot from FIG. 12A showing sub-micron scale structure of mineralized ECM formed by MSCs on PCL/in situ HAPclay (10 wt. %) film.
Figure 12C:
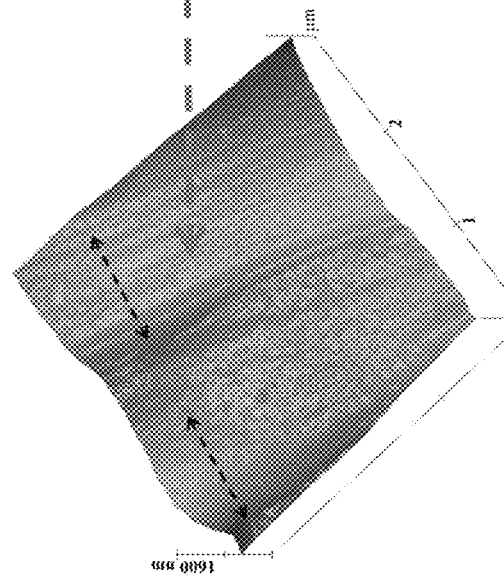
FIG. 12C is an AFM 3D height image/surface plot showing sub-micron scale structure of mineralized ECM formed by MSCs on PCL/in situ HAPclay (10 wt. %) film where the white arrows indicate the formation of "fish scale" packing of mineral particles over collagen fibrils characteristic of human bone, and the solid white lines with a dotted arrow at the center indicate orientations of different groups of collagen fibrils.
Figure 12D:
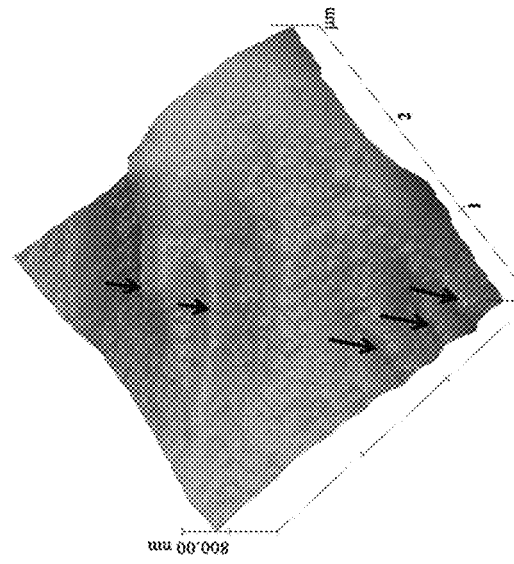
FIG. 12D is a phase image of a region of the AFM 3D height image/surface plot from FIG. 12C showing sub-micron scale structure of mineralized ECM formed by MSCs on PCL/in situ HAPclay (10 wt. %) film.

Phase contrast images were prepared and which indicate the formation of mineralized nodules on PCL/in situ HAPclay films without osteogenic supplements used for differentiation of MSCs. The formation of mineralized nodules by MSCs was confirmed by positive staining of the nodules by Alizarin Red S dye. FIGS. 11A-B show phase contrast images of Alizarin Red S stained PCL/in situ HAPclay (10 wt %) film seeded with human MSCs (culture time 41 days). This indicates the formation of a mineralized extracellular matrix. One of the irregularly shaped regions of intense red color in FIG. 11A is delineated by dotted line may possibly be mineralized ECM in cell nodules/clusters having higher calcium concentration.

Viability and differentiation assays showed that the chitosan-polygalactouronic acid/in situ HAP-clay scaffolds were favorable for viability and differentiation of human MSCs. In addition, the hierarchical structures of initial bone formation as indicated by mineralized fibrillar structure were also observed (see FIGS. 12A-D). FIGS. 12A-D provide AFM 3D height images/surface plots and phase imaging showing sub-micron scale structure of mineralized ECM formed by MSCs on PCL/in situ HAPclay (10 wt. %) films. These figures indicate the formation of collagen fibril bundles, orientation of different groups of collagen fibrils, and formation and packing of mineral particles over the fibrils, which is indicative of human bone formation.

In addition to favorable cellular response indicated by the MTT and ALP assays, the formation of hierarchical mineralized fibrillar structures was also observed providing further evidence of biomineralization facilitated by vesicular delivery (FIG. 8C), which indicates a true bone-mimetic environment. Nanoindentation tests on the bone nodules reveal mechanical properties similar to human bone.

Example 2 demonstrates that the MSCs proliferated in the scaffolds, differentiated into the various cell types and made bone tissue that had the structure and properties similar to the human bone. The nanocomposite material used in the scaffold provided the stimuli for differentiation of the MSCs and required no additional externally supplied growth factors. This indicates that when the scaffold is introduced in vivo, no external growth factors may be required for tissue regeneration in some instances, thus dramatically reducing the complexity of the procedure. Further investigation also revealed that the mechanism of bone formation in the scaffolds is identical to the bone formation mechanism observed in the human bone.

This further indicates that autologous treatments may be possible by harvesting adult stem cells from a patient and using those cells in the treatment of a bone injury or defect according to the methods of the invention.

Example 3

Amino Acid Chain Length Studies

Figure 13A:
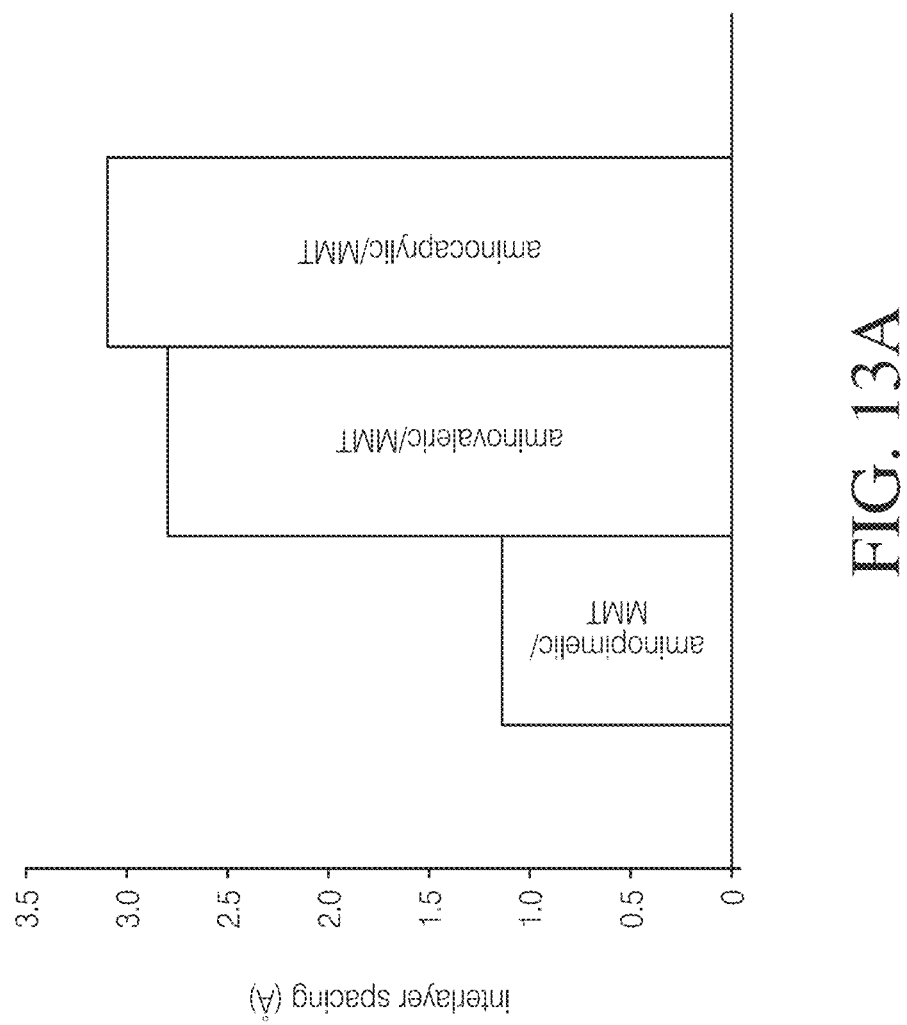
FIG. 13A provides a bar graph representation of XRD data.
Figure 13B:
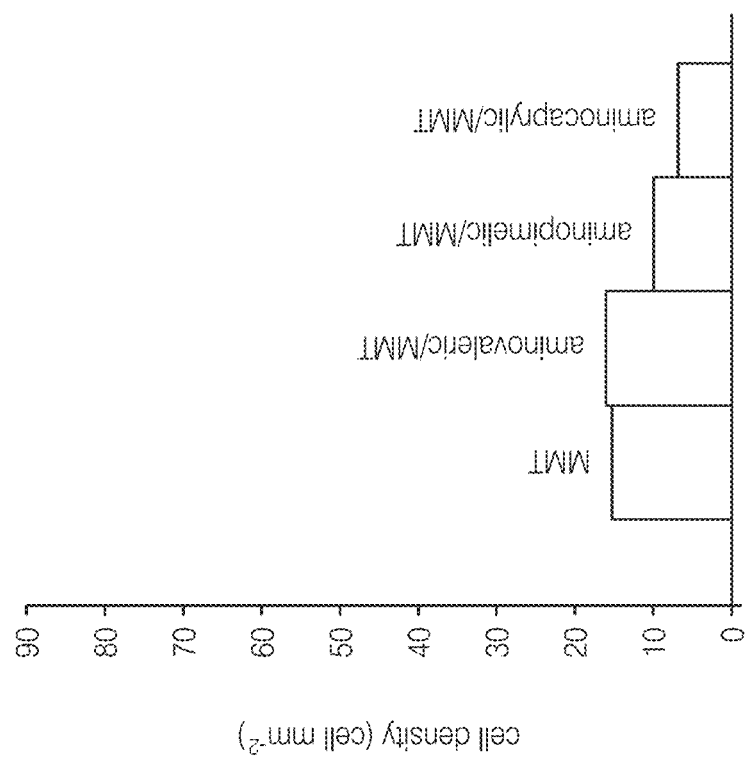
FIG. 13B provides a bar graph representation of MTT assay data.

Three unnatural amino acids were selected to evaluate the impact of chain length on biocompatibility. This was done using human osteoblast cells on clay modified with aminovaleric, amino caprylic and amino pimelic acids. X-ray diffraction (XRD) and a cell proliferation assay (MTT) were performed. All three showed intercalation with XRD indicating an increase in d-spacing of clays (FIG. 13A). FIG. 13A shows interlayer spacing obtained from XRD data indicates increase in interlayer spacing for all three amino acids as compared to bare montmorillonite spacing. The cell proliferation assay (MTT) indicates excellent biocompatibility for all three (FIG. 13B). FIG. 11(b) cell density obtained from MTT assay for human osteoblasts on nanoclay-amino acid polymer films. Cellular response with osteoblast also shows a favorable response. This confirms that in certain embodiments it is preferable to have an amino acid having a longer carbon backbone.

REFERENCES

1. Ambre A H, Katti D R, Katti K S. "Biomineralized hydroxyapatite nanoclay composite scaffolds with polycaprolactone for stem cell-based bone tissue engineering," *Journal of Biomedical Materials Research: Part A,* 103(6), pp. 2077-2101 (2015).
2. Katti D R, Sharma A, Ambre A H, Katti K S. "Molecular interactions in biomineralized hydroxyapatite amino acid modified nanoclay: In silica design of bone biomaterials," *Materials science* & Engineering: Part C Materials for Biological Applications; 46:207-17 (2015).
3. Katti K S, Ambre A H, Peterka N, Katti D R. "Use of unnatural amino acids for design of novel organomodified clays as components of nanocomposite biomaterials," *Philosophical Transactions of the Royal Society of Mathematical Physical and Engineering Sciences* 368:1963-1980 (2010).
4. Ambre A H. "Nanoclay Based Composite Scaffolds For Bone Tissue Engineering Applications," *Journal of Nanotechnology for Engineering and Medicine*, Volume 1: ASME; (2010).
5. Ambre A, Katti K S, Katti D R. "In situ mineralized hydroxyapatite on amino acid modified nanoclays as novel bone biomaterials," *Materials Science* & Engineering: Part C Materials for Biological Applications 31(5): 1017-1029 (2011).

The above specification provides a description of the manufacture and use of the disclosed compositions and methods. Since many embodiments can be made without departing from the spirit and scope of the invention, the invention resides in the claims.

What is claimed is:

1. A composition comprising:
   a polymer,
   from 10 wt. % to 20 wt. % of a clay modified with hydroxyapatite and an amino acid,
   wherein the hydroxyapatite is grown inside the clay using the amino acid,
   wherein the amino acid has a chain length of at least five carbon atoms,
   wherein the polymer is biocompatible, wherein the polymer and clay form a scaffold,
   wherein the scaffold is coated with a bone morphogenetic protein, and
   wherein the scaffold is formed into one or more geometrically interlocking scaffold blocks.

2. The composition of claim 1, wherein the polymer is a natural polymer, synthetic polymer, or a blend, combination, and/or mixture thereof; and wherein the polymer is optionally biodegradable and/or conductive.

3. The composition of claim 2, wherein the polymer comprises albumin, alginate, cellulose, chitin, chitosan, collagen, gelatin, heparin, regenerated silk polymer, polysaccharide, poly(amino acid), polyanhydride, polyester, poly (alpha-hydroxy acid), poly(lactone), poly(orthocarbonate), poly(orthoester), poly(phosphoester), polyphosphazenes, or a blend, mixture, and/or combination thereof.

4. The composition of claim 3, wherein the polymer comprises polyacrylonitrile, polycaprolactone, poly(delta-valerolactone), poly(1,5-dioxepan-2-one), poly(epsilon-caprolactone), poly(ester urethane), polygalactouronic acid, poly(gamma-butyrolactone), polyglycolic acid, poly(alpha-hydroxy acids), polyhydroxyalkanoate, polyhydroxybutyric acid, poly(3-hydroxybutyrate-co-3-hydroxyvalerate, polyimide, polylactic acid, poly(lactic-co-glycolic acid), poly (lactic acid-co-caprolactone), poly(trimethylene carbonate), poly-8-valerolactone, or blends, combinations, or mixtures of the same.

5. The composition of claim 3, wherein the polymer comprises chitosan-polygalactouronic acid, polycaprolactone, or a blend, combination, or mixture thereof.

6. The composition of claim 1, wherein the clay comprises a smectite.

7. The composition of claim 6, wherein the clay comprises bentonite, beidellite, hectorite, montmorillonite, nontronite, saponite, or combinations thereof.

8. The composition of claim 7, wherein the clay comprises sodium bentonite, calcium bentonite, potassium bentonite, sodium montmorillonite, calcium montmorillonite, or combinations thereof.

9. The composition of claim 1, wherein at least two scaffold blocks are interconnected through geometrical interlocking.

10. The composition of claim 1, wherein the polymer comprises between 0.1 wt. % to 99.5 wt. % of the scaffold or the scaffold block.

11. The composition of claim 10, wherein the scaffold or the scaffold block further comprises an additional ingredient of an amino acid, anesthetic, antibiotic, antiangiogenic agent, antibody, anticoagulant, antineoplastic agent, antiviral agent, biomaterial, carbohydrate, cell, cytotoxic agent, drug, electrolyte, growth factor, immunomodulator, inorganic material, lipid, mineral, oligonucleotide, osteoblast, osteoclast, osteo stem cell, polypeptide, progenitor, protein, therapeutic agent, tissue, tissue or cell aggregate, vasoactive agent, or combinations thereof.

12. The composition of claim 11, wherein the additional ingredient is between 0.01 wt. % and 50 wt. % of the composition.

13. The composition of claim 12, wherein the additional ingredient is attached to, coats, or modifies the scaffold, scaffold block, clay, and/or polymer.

14. The composition of claim 12, wherein the additional ingredient is impregnated in the scaffold or the scaffold block.

15. The composition of claim 12, wherein the composition is for treating bone injuries and/or defects.

16. The composition of claim 15, wherein one or more of the additional ingredients is released by a controlled release and/or sustained release.

17. The composition of claim 12, wherein the additional ingredient comprises one or more of a human osteoblast, a non-human animal species osteoblast, an amino acid, a growth factor, a bone morphogenic protein, a hydroxyapatite mineral, and/or an adult stem cell.

18. The composition of claim 1, wherein the scaffold block has at least two dimensions that are between 0.1 millimeters and 50 millimeters.

19. The composition of claim 1, wherein the scaffold block has three dimensions that are less than 50 millimeters.

\* \* \* \* \*